US007429377B2

(12) United States Patent
Artamonov et al.

(10) Patent No.: US 7,429,377 B2
(45) Date of Patent: Sep. 30, 2008

(54) THERAPEUTIC COMPOSITION CONTAINING A PLURALITY OF IMMOBILIZED PROTEASES

(75) Inventors: Andrei Vladimirovich Artamonov, Novosibirsk (RU); Evgeny Ivanovich Vereschagin, Novosibirsk (RU); Oleg Vitalievich Grishin, Novosibirsk (RU); Alexandr Vasilievich Troitsky, Novosibirsk (RU)

(73) Assignee: Zakrytoe Aktsionernoe Obschestvo "Aksis", Novosibirsk (RU)

( * ) Notice: Subject to any disclaimer, the term of this patent is extended or adjusted under 35 U.S.C. 154(b) by 344 days.

(21) Appl. No.: 10/498,839

(22) PCT Filed: Dec. 24, 2002

(86) PCT No.: PCT/RU02/00552

§ 371 (c)(1),
(2), (4) Date: Jun. 14, 2004

(87) PCT Pub. No.: WO03/059326

PCT Pub. Date: Jul. 24, 2003

(65) Prior Publication Data

US 2005/0220780 A1    Oct. 6, 2005

(30) Foreign Application Priority Data

Dec. 26, 2001    (RU)    ............... 2001135876

(51) Int. Cl.
*A61K 38/54* (2006.01)
*A61K 38/48* (2006.01)
*A61K 38/46* (2006.01)
*C12N 11/02* (2006.01)
*C12N 11/10* (2006.01)
*C12N 11/08* (2006.01)

(52) U.S. Cl. ................. 424/94.2; 424/94.64; 424/94.67; 435/177; 435/178; 435/180

(58) Field of Classification Search ........................ None
See application file for complete search history.

(56) References Cited

U.S. PATENT DOCUMENTS 5,133,968 A    7/1992    Nakayama et al.

FOREIGN PATENT DOCUMENTS

| GB | 2147206 | 5/1985 |
| RU | 2003346 | 11/1993 |
| RU | 2137835 | 9/1999 |
| RU | 2146139 | 3/2000 |
| RU | 2150936 | 6/2000 |
| RU | 2158603 | 11/2000 |
| RU | 2001135876 | 12/2001 |

OTHER PUBLICATIONS

English Translation of Claims of RU 2150936 Dated Jun. 20, 2000.
English Translation of Claims of RU 2137835 Dated Sep. 20, 1999.
English Translation of Claims of RU 2158603 Dated Nov. 20, 2000.
English Translation of Claims of RU 2146139 Dated Mar. 10, 2000.
English Translation of Claims of RU 2003346 Dated Nov. 30, 1993.
English translation of RU 2001135876, dated Dec. 26, 2001.
Fibrinolytic Therapy Trialists' Collaborative Group. "Indications for fibrinolytic therapy in suspected acute myocardial infarction: collaborative overview of early mortality and major morbidity results from all randomised trials of more than 1000 patients", *The Lancet* (1994), 343: 311-322.
Nassanov, E.L. et al. "Selective Inhibitors of Cyclooxygenase-2: New Prospects of Treating Human Diseases", *Terapevticheskij Arkhiv* (1998), 70(5): 8-14. English translation of p. 9, paragraph 2.
Brottier, L. et al. "Therapeutic value of a cardioprotective agent in patients with severe ischaemic cardiomyopathy", *European Heart Journal* (1990), 11: 207-212.
Salganik, R.I. et al. "Immobilized Proteolytic Enzymes in Treating Purulent-Necrotic Processes", *Novosibirsk* (1981), pp. 3-8. English translation of p. 5, paragraph 2, and p. 6, paragraphs 1-2.
Peretyagin, O.A. "Effectiveness of Using Immobilized Proteolytic Enzyme Immozyne in Treating Severe Chemical Burns of the Cornea in Experiment", *Oftalmologiya* (1987), No. 3: 145-148. English translation of p. 145, 147.
Gonchar, A. M. et al. "The Application of Immobilized Enzymes for Complex Treatment of Purulent Dieases", *Veterinariya* (1989), No. 4: 52-55. English translation of p. 52.
"ACC/AHA Guidelines for the Management of Patients with Acute Myocardial Infarction", Collection of Papers, *Novosibirsk* (1999), p. 100, 120-121, 148. English translation of p. 120, paragraph 2.

*Primary Examiner*—David M. Naff
(74) *Attorney, Agent, or Firm*—Ladas and Parry LLP

(57) ABSTRACT

A pharmaceutical composition having thrombolytic, anti-inflammatory and cytoprotective properties is described. The composition contains active proteases attached to a gel or to a mixture of a gel with a water-soluble polymer, said attachment being achieved with the help of radiation, preferably with the help of gamma-radiation or a flow of accelerated electrons. As the proteases the composition contains proteases which are stable at a temperature of up to 70° C., preferably at 30-40° C., for instance such as subtilysine, trypsin, chemotrypsin, papain or streptokinase. The gel is preferably polyethylene glycol gel, dextran gel, or polyglycane gel, and the water-soluble polymer is polyethylene glycol, polyvinyl alcohol, dextran or polyglycane. The method of preparing said composition and its use are also disclosed. The composition has a broad range of application, and can be used in cardiology, nephrology, surgery, rheumatology, gynecology and gastroenterology.

11 Claims, 4 Drawing Sheets

THERAPEUTIC COMPOSITION CONTAINING A PLURALITY OF IMMOBILIZED PROTEASES

FIELD OF THE ART

The present invention relates to medicine, particularly to pharmacology and drugs based on enzyme preparations, and can be used in complex therapy for treating ischemic heart disease, ischemic cerebral strokes, rheumatoid processes and other diseases accompanied by ischemic, thrombotic, and non-specific inflammation phenomena.

This invention encompasses the field of enzymatic hydrolysis of thrombogenic proteins, mainly fibrin, structure-forming protein of all thrombi, irrespective of the location and size of peptides. More particularly, the invention relates to compounds containing proteolytic enzymes possessing fibrinolytic properties, immobilized on (attached to) hydrophilic water-soluble polymers. The invention is also associated with methods of using such compounds for fibrinolytic therapy in treating acute myocardial infarctions, ischemic cerebral strokes, and also with therapeutic methods directed to the correction (improvement) of hemorheological characteristics in treating ischemic injuries of organs and tissues of different etiology, including microthrombosis.

STATE OF THE ART

Known in the art are various medicinal preparations used for treating ischemic heart disease and ischemic cerebral strokes. As a rule, at the final stage of these diseases the main pathogenetic factor is intravascular thrombosis. In present-day medical practice thrombolytic medicinal preparations have become widely used as etiotropic therapy means for treating acute myocardial infarctions and ischemic cerebral strokes. There are known pharmaceutical preparations, such as streptase, streptokinase, tissue plasminogen activator (alteplase) and fibrinolysine (Methodological Recommendations for Carrying out Early Therapeutic Measures in Patients with Acute Myocardial Infarction, Communication of the American Cardiologic College and American Heart Association. V. N. Ganyukov (Ed.), Collection of Papers, Novosibirsk, 1998, p. 100 (Russian translation)). All these preparations, directly or as a result of activation of the anticoagulative system of blood, act on fibrin, leading to its destruction and, correspondingly, to lysis of the intravascular thrombus. In spite of their high therapeutic effectiveness, these preparations have a pronounced side effect, namely, they can induce uncontrollable and dangerous hemorrhages, due to depletion of the coagulative system of blood (Saunders W. B. Indications for Fibrinolytic Therapy Trialists Collaborative Group.//Lancet Ltd., 1994, vol. 343, pp. 311-322). Besides, for such preparations as streptokinase and alteplase it is difficult to select an adequate therapeutic dosage, because of the existence of an individual antiserum activity to streptococcus in the human organism, that leads to the inactivation of these preparations.

Medicinal preparations are known, which are capable of diminishing the inflammatory reaction. The most widespread of these preparations are non-steroidal anti-inflammatory preparations, such as aspirin, indomethacin, sodium diclofenac, and others (Nasonov E. L., Tsvetkova V. S., and Tov N. L., Selective inhibitors of cyclooxygenase-2: new prospects of treating human diseases//Ter. Arkhiv, 1998, No. 5, pp. 8-14 (in Russian)). The known pharmaceutical preparations are not free from essential disadvantages: they may cause stomach injuries with development of non-steroidal gastropathy, hemorrhages and ulcerations of the gastrointestinal tract mucosa.

Pharmaceutical preparations are known, which have cytoprotective properties, such as preductal (cardioprotective effect) and blockers of $H_2$ receptors (gastrozepine, ranitidine). The known preparations have a weak cytoprotective effect and prove to display pharmacological action on prolonged administration (Brottier L., Barat J. L., Combie C. et al., Therapeutic value of a cardioprotective agent in patients with severe ischaemic cardiomyopathy//Eur. Heart J., 1990, vol. 11, pp. 207-212).

At present no data can be found in scientific and medical literature concerning the provision of pharmaceutical compositions producing multipurpose synergic effect on the main pathogenetic links of ischemia, inflammation and thrombosis in combination with cytoprotective properties.

Different methods for the immobilization of enzymes, including proteases, on a number of polymeric carriers were reported. For instance, in the work by R. I. Salganik et al. "Immobilized Proteolytic Enzymes in Treating Purulent Processes", Novosibirsk, pp. 3-8, 1981 (in Russian) a method is described for treating purulent wounds, abscesses and phlegmons with the help of proteolytic enzymes attached covalently to solid granules of cellulose. The use of liquid polymers with attached proteases is described by O. A. Peretyagin et al. in "Oftalmologiya", 1987, No. 3, pp. 145-148 and by Gonchar et al. in "Veterinariya", 1989, No. 4, pp. 52-55. In most cases a bifunctional chemical reagent was used as the binding agent, in which one chemical group was linked to the amino acid residue of the enzyme protein, while another reactive group was linked to the polymeric carrier. A number of chemical procedures for the covalent attachment of various proteins to solid carriers were investigated. However, proteases attached to solid granules or fibers cannot be used for treating injuries or diseases which lead to intravascular thrombosis and are accompanied by negative changes of hemorheology in the microcirculatory channel of tissues and organs.

Therefore, compounds are required, which effectively hydrolyze proteins, predominantly those responsible for thrombosis in blood vessels of different diameters, which constitute an etiological factor of the development of such diseases as acute myocardial infarction and ischemic cerebral stroke. At present such compounds containing nontoxic thrombolytics and substances with hemorheological corrective functions have not been synthesized for complex therapy of ischemic heart disease, hypertensive disease and rheumatoid diseases. Simple, inexpensive and convenient methods are also required for simultaneously attaching proteases to a complex of polymeric carriers and providing sterilization of the end product. Ideal methods are those which can provide compounds having different viscosity and aggregate state, suitable for different purposes and different ways of administration.

ESSENCE OF THE INVENTION

The herein-presented investigation meets the above-said requirements and also offers relative advantages over other medicinal preparations and methods of preparing pharmaceutical compositions featuring a complex synergic therapeutic effect on various links of the pathogenesis of ischemic heart disease. The presented investigation, the claimed pharmaceutical composition, and methods of preparing thereof ensure the obtaining of high therapeutic effect in treating non-specific inflammatory processes owing to cytoprotective, thrombolytic and anti-ischemic effects.

The proposed invention is directed to the provision of compositions for selective hydrolysis of thrombogenic proteins, consisting of active proteases attached to a combination of hydrophilic water-soluble polymers. Said compositions predominantly consist of subtilysines immobilized on hydrophilic polymers.

This invention contributes to the development of methods of making such compositions by attaching proteases to water-soluble polymers to produce a mixture and simultaneously sterilize said mixture by irradiation, particularly with the help of a stream of accelerated electrons or gamma-radiation, as well as other kinds of ionizing radiation, including laser radiation sources.

The proposed invention is directed to novel pharmaceutical compositions for the hydrolysis of thrombogenic proteins, consisting of active proteases attached to hydrophilic polymers. Such compositions are useful for the removal of thrombi comprising fibrin and other formations. The proposed invention is also directed to novel compounds for correcting pathological changes in tissues and organs, originated as a result of thrombosis and ischemia, as well as to the correction of non-specific inflammatory reactions, and as an auxiliary means for treating and preventing gastropathies developing as a result of administering non-steroidal anti-inflammatory preparations. Proteases immobilized on hydrophilic polymers according to the invention selectively degrade thrombogenic proteins, mainly fibrin, while live cells and functionally active proteins remain intact and undamaged. For effective hydrolysis of the proteins of thrombotic masses, it is preferable to have a polyfunctional mixture of proteases which are capable of recognizing and hydrolyzing various peptide linkages. Natural proteases include, for instance, subtilysine, trypsin, chemotrypsin, papain and other enzymes of animal and bacterial origin, having fibrinolytic and proteolytic activity.

Though proteases are obtainable from any sources, including animal and vegetable ones, bacterial proteases are especially preferable. Compared with other types of proteases, bacterial proteases are usually less costly and are available in unlimited amounts. Preferable bacterial proteases of the proposed invention can be reproduced. by *Bac. subtilis* and are known as subtilysines. A mixture of neutral and/or alkaline subtilysines is preferable, because the mixture can selectively degrade a variety of peptide linkages and preserve activity at pH from 6.0 to 10.0.

The proteases according to the proposed invention are attached to a combination of water-soluble polymers which act as carriers for proteolytic enzymes. Preferable water-soluble polymers are polyethylene oxide (PEO), synonym: polyethylene glycol (PEG), having a molecular weight of 1500 kDa (PEO-1500), and dextran having a molecular weight of 30-40 kDa. Polyethylene oxides and dextrans having a smaller or greater molecular weight can also be used instead of or together with PEO-1500 and dextran having a molecular weight of 30-40 kDa. Other suitable water-soluble polymers and their combinations that also can be used include, e.g., polyvinyl alcohol, polyvinylpyrrolidone, and the like.

The compositions according to the proposed invention can be in any non-solid or solid form or in a combination of aggregate forms. It is preferable to use lyophilized powders (substances) in various combinations with water-soluble polymers as the compositions, depending on the field in which the compound is planned to be used.

For the provision of the overall therapeutic properties, antibodies, therapeutic disinfectants, glucocorticoids, tissue regeneration stimulants, and other therapeutic agents can be added to the given composition. To the benefit of the case in hand, such agents should not be mixed in a considerable amount with proteases, unless their effect on the specific and therapeutic activity of the claimed pharmaceutical composition has been circumstantiated (investigated).

The present invention is also directed to methods of preparing compositions by attaching proteases to water-soluble polymers and simultaneously sterilizing the mixture by radiation. Preferable kinds of radiation are accelerated electrons or gamma-radiation.

Briefly, the technology is as follows: a solution of a mixture of proteases, preferably subtilysines, and water-soluble polymers, preferably polyethylene oxide and dextran, is subjected to the action of electrons emitted by an electron accelerator in a dose which promotes attaching thereof to a polymeric carrier and simultaneously sterilizing the obtained compound. On the other hand, gamma-rays emitted by $Co^{60}$ can be used instead of an electron bunch with the provision of attaching and sterilizing the components. A sufficient radiation dose can be selected by a person skilled in the art by calculating the conditions for the provision of the mixture sterility and inessential effect on the proteolytic activity of the enzymes.

Finally, the proposed invention is also directed to methods of cleaning the vascular bed from thrombi by controlling or using effective amounts of the claimed composition for the removal of this material. The compositions according to the present invention are effective when used as preparations for pharmaceutical purposes in different ways and fields, such as medicine, stomatology, veterinary medicine, and personal care.

In this connection, the compositions according to the present invention are particularly eligible for treating ischemic heart disease and its complications, as well as ischemic cerebral strokes, rheumatoid diseases and other pathologies, in whose pathogenesis there take place an inflammatory reaction, ischemia of tissues, disturbances of hemorheology and vascular microcirculation because of thrombosis. The claimed pharmaceutical composition is also suitable for enzymatic destruction of viscous biological fluids, such as secreted mucosae (e.g., bronchial secret), therefore it is effective in treating pulmonary diseases for the prevention and treatment of bronchial obstruction. The claimed pharmaceutical composition is also applicable for the enzymatic destruction of proteins and peptides of necrotic tissues which are always present in traumatic and infectious-inflammatory processes. Therefore this composition is also effective in treating pyoinflammatory diseases of different etiology and localization.

These compositions can be applied to the focus of injury by any method known in the medicine. Such methods include, for instance, parenteral administration, intracavitary and external use, aerosol spraying, syringing through a trocar, catheters, bronchoscope, or other suitable use. The method of administration will depend, at least partially, on the nature of the injured. area and on the type and quantity of thrombogenic or necrotic tissues to be removed. The predominant method of administration is parenteral administration of the preparation (compositions).

The claimed composition in the standard therapeutic dose of 50 physiological units/ml (50 PhU/ml) reliably excels fibrinolysine (p<0.02); trypsin (p<0.01); and spontaneous thrombolysis in physiological solution (p<0.01).

Figure 2:
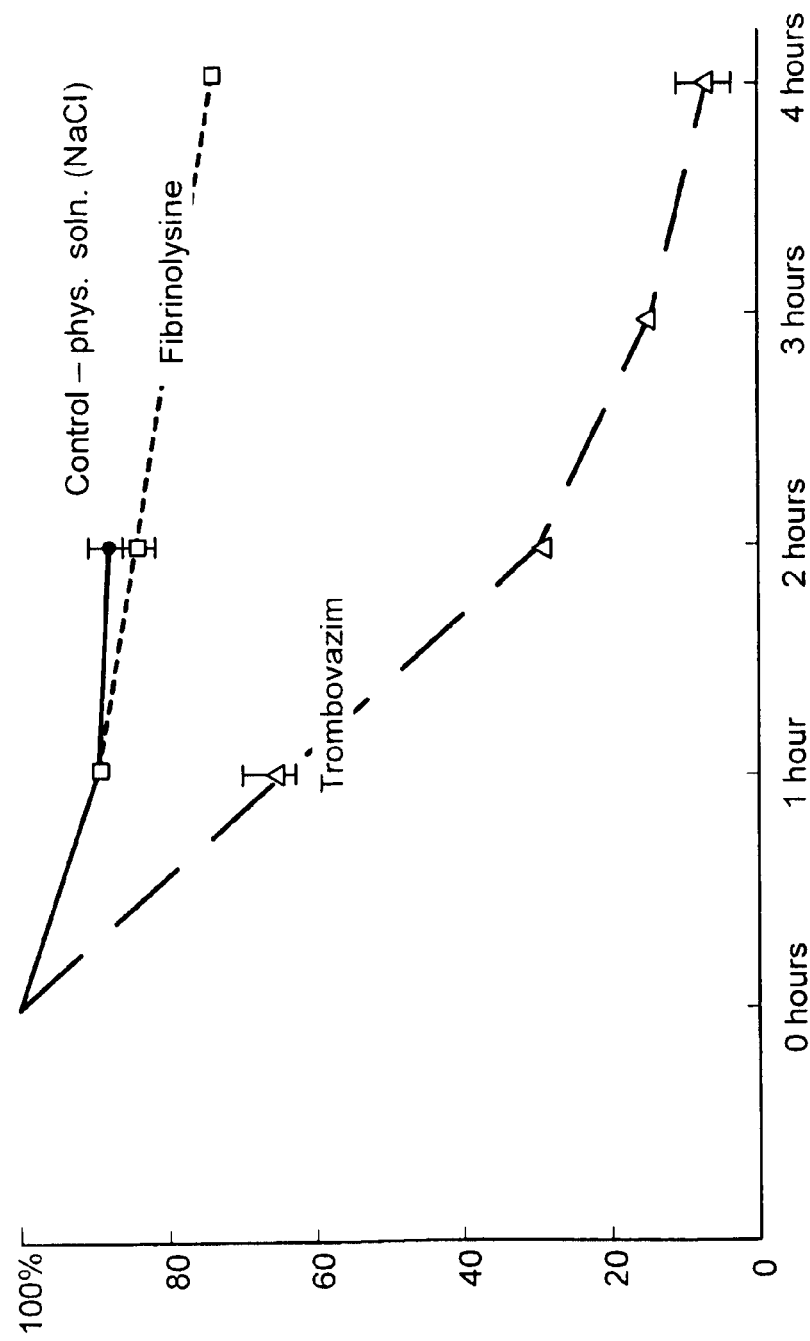

FIG. 2 demonstrates that the thrombolytic properties of the claimed composition are preserved as the thrombus "age" increases to 7 days. Fibrolysine does not act on the 7-days thrombus. During the first two hours the action of fibrolysine does not differ with certainty from the spontaneous background lysis in physiological solution. By the end of the 4th hour the claimed composition dissolves the thrombus completely, while fibrinolysine lyses only 20% of the mass of the "old" thrombus.

Figure 3:
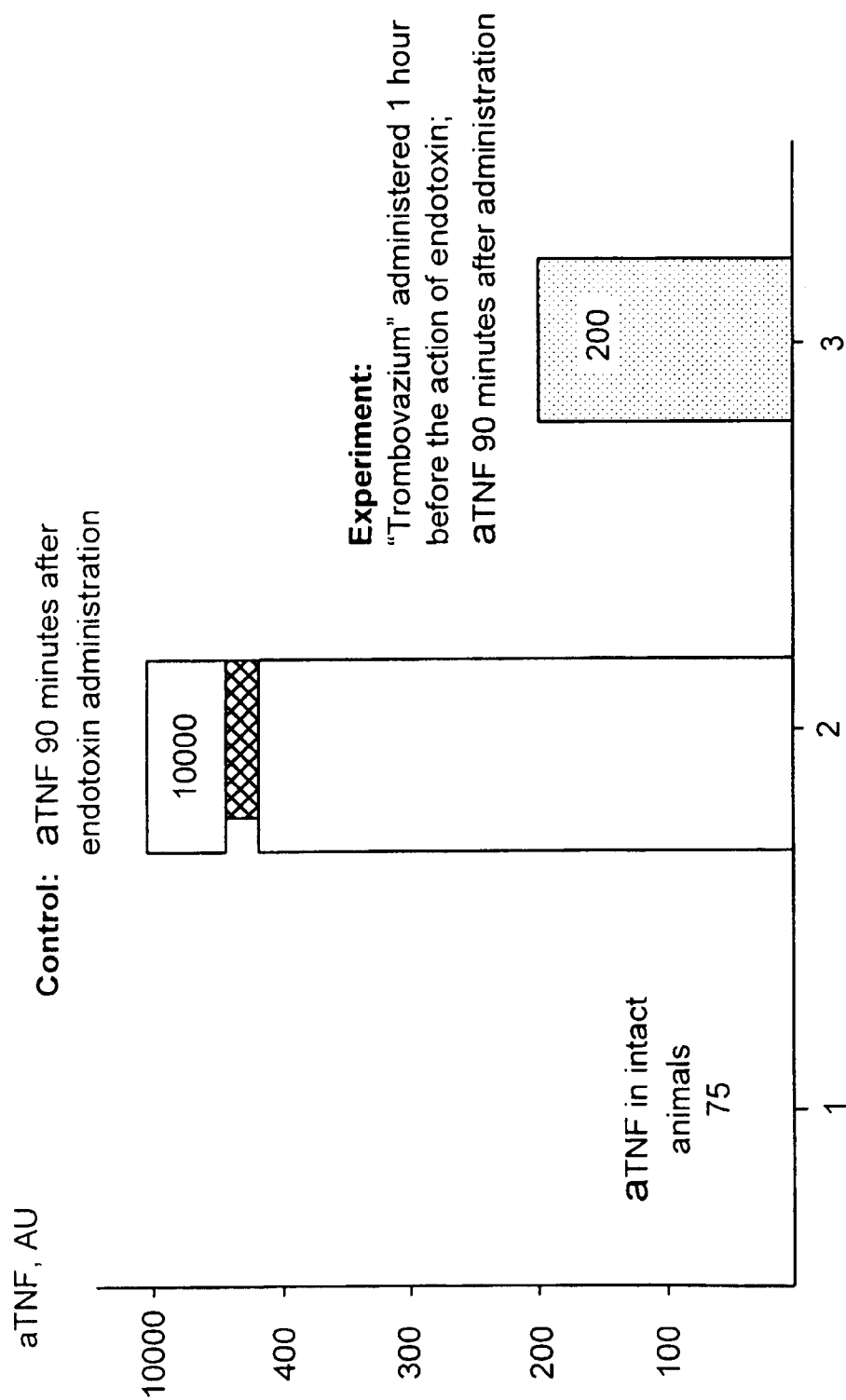

FIG. 3 demonstrates the anti-inflammatory properties of he claimed composition, investigated on a model simulating induction of an inflammation mediator-tumor necrosis factor (αTNF) in CBA-line mice with endotoxic shock. The activity of the αTNF was measured using L929 line cells and was expressed in activity units (AU):

1—αTNF activity in intact animals;
2—αTNF activity in animals after administration of endotoxin;
3—αTNF activity in animals to which the claimed composition was administered one hour before the administration of endotoxin. As is seen, the claimed composition reduces 50-fold the αTNF activity.

Figure 4:
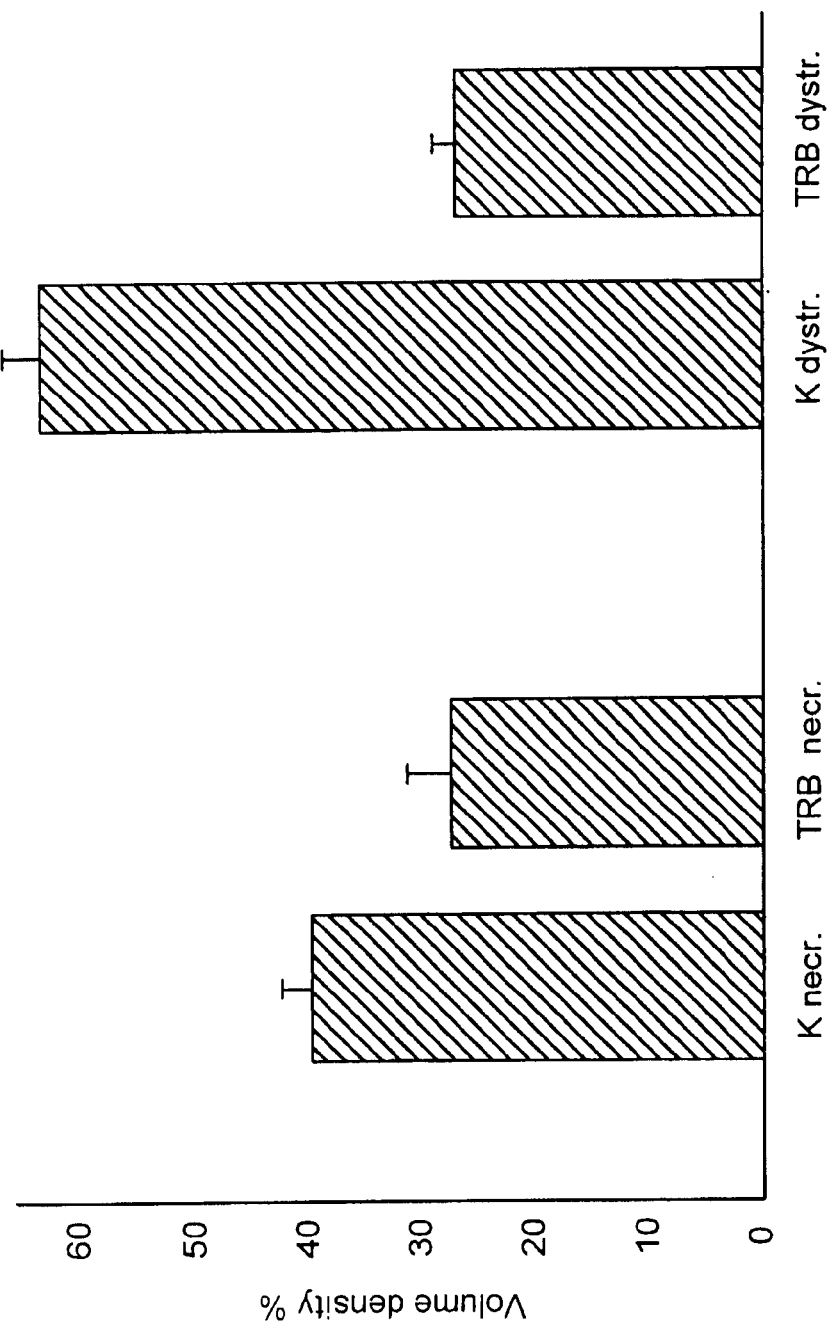

FIG. 4 demonstrates the cytoprotective properties of the claimed composition, studied on a model of adrenaline myocarditis in rats. Data of histological morphometric investigations of the volume of necroses and dystrophic changes in the myocardium of the rats are presented. The volume of injuries was determined planimetrically and expressed in percent of the volume density which is equal to the volume of injuries/total value of tissue ratio multiplied by 100%.

K necr.—control animals to which after administering adrenaline 1 ml of isotonic NaCl solution was administered intraperitoneally twice a day.

TRB necr.—experimental animals to which after administering adrenaline 1 ml of the claimed composition was administered intraperitoneally twice a day.

The first two columns demonstrate positive effect of the claimed composition (approximately 1.5-fold reduction of the number of necroses in the cardiac muscle) by the end of the third day of treating the animals.

The next two columns demonstrate positive effect of the claimed composition (approximately 2.5-fold reduction of the number of dystrophic changes in the cardiac muscle) by the end of the seventh day of treating the animals.

The Examples which follow are intended to illustrate the formulation, the method of preparing and the pharmacological properties of the claimed composition, but not to limit the proposed invention.

PREFERRED EMBODIMENTS OF THE INVENTION

EXAMPLE 1

The proposed pharmaceutical composition is prepared in the following manner:

a reaction mixture is prepared by dissolving protosubtilin, predominantly protosubtilin G3Kh and polyethylene oxide (PEO) having a molecular weight of 400-20000 Da (predominantly 1500 Da) in a solution of dextran having a molecular weight of 40-70 kDa (predominantly 40 kDa) in a 0.025 M sodium phosphate buffer solution with pH 7.5-8.2. The obtained mixture is purified by removing ballast proteins by salt precipitation and subsequent filtration. The resulting solution is subjected to irradiation with gamma-rays or a stream of accelerated electrons (with energy of 2.0 MeV) in a dose of 0.5-1.5 Mrad. The solution after irradiation is subjected to sterilizing filtration and packaged in 10 ml batches into 15 ml vials. Then the solution is lyophilized to a residual moisture content not exceeding 2%.

As a result, a composition is obtained, containing a protease complex from *Bac. subtilis*, immobilized on polyethylene oxide and dextran. The proteolytic activity of the obtained composition in one vial is from 500 to 1000.0 proteolytic units per gram (PU/g). The composition comprises a slightly yellowish porous homogeneous mass.

For therapeutic purposes a solution of the claimed composition is used (conditional appellation thereof being "Trombovazim"), which is prepared ex tempore by dissolving the contents of a vial in 10 ml of sterile isotonic solution of sodium chloride or in 10 ml of water for injections.

EXAMPLE 2

The claimed composition can be prepared by another method, namely, by preparing separately an active component (component (1)) which contains a complex of proteases immobilized on polyethylene oxide and dextran, and a solvent which is a solution of polyethylene oxide (component (2)). The two-component formulation of the composition makes it possible to vary the activity of the claimed pharmaceutical composition by varying the active component/solvent ratio, so that individual schemes of treating can be selected. The two-component composition is prepared in the following manner:

Component (1) (Active Substance)

The reaction mixture is prepared by dissolving protosubtilin (predominantly protosubtilin G3Kh) and polyethylene oxide (PEO) having a molecular weight of 400-20000 Da (predominantly 1500 Da) in a solution of dextran having a molecular weight of 70-40 kDa (predominantly 40 kDa) in a 0.025 M sodium phosphate buffer solution with pH 7.5-8.2. The obtained mixture is purified by removing ballast proteins by salt precipitation and subsequent filtration. The resulting solution is subjected to irradiation with gamma-rays or a stream of accelerated electrons (with energy of 2.0 MeV) in a dose of 1.0 Mrad. The solution after irradiation is subjected to sterilizing filtration and packaged in 10 ml batches into 15 ml vials. Then the solution is lyophilized to a residual moisture content not exceeding 2%.

As a result, component (1) of the composition is obtained, which component contains a protease complex from *Bac. subtilis*, immobilized on polyethylene and dextran. The proteolytic activity of the obtained composition is from 500 to 1000.0 PU/g. Component (1) comprises a porous slightly yellowish homogeneous mass.

Component (2) (Solvent)

A solution of polyethylene oxide (predominantly polyethylene oxide with a molecular weight of 1500 Da) is prepared in a 0.025 M sodium phosphate buffer solution with pH 7.5-8.2. The obtained solution is subjected to irradiation with gamma-rays or a stream of accelerated electrons (with energy of 2.0 MeV) in a dose of 1.0 Mrad. The solution after irradiation is subjected to sterilizing filtration and packaged in 10 ml batches into 15 ml vials.

As a result, a sterile solvent for component (1) of the claimed composition is obtained. The solvent comprises a slightly yellowish liquid.

For therapeutic purposes a solution of the claimed composition is used (conditional appellation thereof being "Trombovazim"), which is prepared ex tempore by dissolving the contents of a vial with component (1) containing immobilized proteases in 10 ml of component (2) (solvent).

Dissolution ex tempore of component (1) in the solvent (component (2)) gives the claimed pharmaceutical composition.

EXAMPLE 3

15 of polyethylene oxide PEO-1500 are dissolved in 300 ml of a 10% solution of dextran having a molecular weight of 40 kDa in a 0.025 M sodium phosphate buffer with pH 7.5, 6.3 g of protosubtilin G3Kh are added, the mixture is stirred at a temperature of 18-20° C. for 30 minutes. Then ballast proteins are precipitated by salt precipitation techniques. For this to be done, added to the mixture in succession till complete dissolution are 1.3 g of sodium phosphate disubstituted to final concentration of 0.45% and 1.9 g of calcium chloride to final concentration of 0.63%. After the dissolution of calcium chloride an insoluble precipitate of calcium phosphate is formed in the reaction mixture, and this calcium phosphate adsorbs the ballast proteins. The mixture is maintained for 12 hours at a temperature of 4 to 8° C. for complete precipitation of the ballast proteins. After that the reaction mixture is filtered through paper filters ("white ribbon"). The volume of the filtrate is 300 ml. The obtained solution is subjected to gamma irradiation in a dose of 1.0 Mrad. After the irradiation the solution is subjected to sterilizing filtration, packaged in batches of 10 ml in 15 ml vials and lyophilized to a residual moisture content not exceeding 2%. As a result, a composition is obtained, having the following formulation in weight percent:

| 1. | Protosubtilin G3Kh | 2.1 |
| 2. | Dextran (molecular weight 40 kDa) | 10.0 |
| 3. | Polyethylene oxide PEO-1500 | 5.0 |
| 4. | 0.025 M sodium phosphate buffer | 82.9 |

The proteolytic activity of the composition is 850 PU/g.

EXAMPLE 4

15 of polyethylene oxide PEO-1500 are dissolved in 300 ml of a 5% solution of dextran having a molecular weight of 40 kDa in a 0.025 M sodium phosphate buffer with pH 8.2, 6.0 g of protosubtilin G3Kh are added, the mixture is stirred at a temperature of 18-20° C. for 30 minutes. Then ballast proteins are precipitated by salt precipitation techniques. For this to be done, added to the mixture in succession till complete dissolution are 1.3 g of sodium phosphate disubstituted to final concentration of 0.45% and 1.9 g of calcium chloride to final concentration of 0.63%. After the dissolution of calcium chloride an insoluble precipitate of calcium phosphate is formed in the reaction mixture, and this calcium phosphate adsorbs the ballast proteins. The mixture is maintained for 12 hours at a temperature of 4 to 8° C. for complete precipitation of the ballast proteins. After that the reaction mixture is filtered through paper filters ("white ribbon"). The volume of the filtrate is 300 ml. The obtained solution is subjected to gamma irradiation in a dose of 1.0 Mrad. After the irradiation the solution is subjected to sterilizing filtration, packaged in batches of 10 ml in 15 ml vials and lyophilized to a. residual moisture content not exceeding 2%. As a result, a composition is obtained, having the following formulation in weight percent:

| 1. | Protosubtilin G3Kh | 2.0 |
| 2. | Dextran (molecular weight 40 kDa) | 5.0 |
| 3. | Polyethylene oxide PEO-1500 | 5.0 |
| 4. | 0.025 M sodium phosphate buffer | 88.0 |

EXAMPLE 5

0.5 of polyethylene oxide PEO-1500 is dissolved in 300 ml of a 10% solution of dextran having a molecular weight of 40 kDa in a 0.025 M sodium phosphate buffer with pH 8.2, 5.7 g of protosubtilin G3Kh are added, the mixture is stirred at a temperature of 18-20° C. for 30 minutes. Then ballast proteins are precipitated by salt precipitation techniques. For this to be done, added to the mixture in succession till complete dissolution are 1.3 g of sodium phosphate disubstituted to final concentration of 0.45% and 1.9 g of calcium chloride to final concentration of 0.63%. After the dissolution of calcium chloride an insoluble precipitate of calcium phosphate is formed in the reaction mixture, and this calcium phosphate adsorbs the ballast proteins. The mixture is maintained for 12 hours at a temperature of 4 to 8° C. for complete precipitation of the ballast proteins. After that the reaction mixture is filtered through paper filters ("white ribbon"). The volume of the filtrate is 300 ml. The obtained solution is subjected to gamma irradiation in a dose of 1.0 Mrad. After the irradiation the solution is subjected to sterilizing filtration, packaged in batches of 10 ml in 15 ml vials and lyophilized to a residual moisture content not exceeding 2%. As a result, a composition is obtained, having the following formulation in weight percent:

| 1. | Protosubtilin G3Kh | 1.9 |
| 2. | Dextran (molecular weight 40 kDa) | 10.0 |
| 3. | Polyethylene oxide PEO-1500 | 0.5 |
| 4. | 0.025 M sodium phosphate buffer | 87.6 |

The proteolytic activity of the composition is 750 PU/g.

EXAMPLE 6

15 of polyethylene oxide PEO-1500 are dissolved in 300 ml of a 5% solution of dextran having a molecular weight of 40 kDa in a 0.025 M sodium phosphate buffer with pH 8.2, 7.5 g of protosubtilin G3Kh are added, the mixture is stirred at a temperature of 18-20° C. for 30 minutes. Then ballast proteins are precipitated by salt precipitation techniques. For this to be done, added to the mixture in succession till complete dissolution are 1.3 g of sodium phosphate disubstituted to final concentration of 0.45% and 1.9 g of calcium chloride to final concentration of 0.63%. After the dissolution of calcium chloride an insoluble precipitate of calcium phosphate is formed in the reaction mixture, and this calcium phosphate adsorbs the ballast proteins. The mixture is maintained for 12 hours at a temperature of 4 to 8° C. for complete precipitation of the ballast proteins. After that the reaction mixture is filtered through paper filters ("white ribbon"). The volume of the filtrate is 300 ml. The obtained solution is subjected to gamma irradiation in a dose of 1.2 Mrad. After the irradiation the solution is subjected to sterilizing filtration, packaged in batches of 10 ml in 15 ml vials and lyophilized to a residual moisture content not exceeding 2%. As a result, a composition is obtained, having the following formulation in weight percent:

| 1. | Protosubtilin G3Kh | 2.5 |
|---|---|---|
| 2. | Dextran (molecular weight 40 kDa) | 5.0 |
| 3. | Polyethylene oxide PEO-1500 | 5.0 |
| 4. | 0.025 M sodium phosphate buffer | 87.5 |

The proteolytic activity of the composition is 500 PU/g.

EXAMPLE 7

15 of polyethylene oxide PEO-4000 are dissolved in 300 ml of a 5% solution of dextran having a molecular weight of 70 kDa in a 0.025 M sodium phosphate buffer with pH 8.2, 7.5 g of protosubtilin G10Kh are added, the mixture is stirred at a temperature of 18-20° C. for 30 minutes. Then ballast proteins are precipitated by salt precipitation techniques. For this to be done, added to the mixture in succession till complete dissolution are 1.3 g of sodium phosphate disubstituted to final concentration of 0.45% and 1.9 g of calcium chloride to final concentration of 0.63%. After the dissolution of calcium chloride an insoluble precipitate of calcium phosphate is formed in the reaction mixture, and this calcium phosphate adsorbs the ballast proteins. The mixture is maintained for 12 hours at a temperature of 4 to 8° C. for complete precipitation of the ballast proteins. After that the reaction mixture is filtered through paper filters ("white ribbon"). The volume of the filtrate is 300 ml. The obtained solution is subjected to gamma irradiation in a dose of 0.8 Mrad. After the irradiation the solution is subjected to sterilizing filtration, packaged in batches of 10 ml in 15 ml vials and lyophilized to a residual moisture content not exceeding 2%. As a result, a composition is obtained, having the following formulation in weight percent:

| 1. | Protosubtilin G10Kh | 2.5 |
|---|---|---|
| 2. | Dextran (molecular weight 70 kDa) | 5.0 |
| 3. | Polyethylene oxide PEO-4000 | 5.0 |
| 4. | 0.025 M sodium phosphate buffer | 87.5 |

The proteolytic activity of the composition is 1000 PU/g.

EXAMPLE 8

Preparing the Claimed Composition Consisting of an Active Component and a Solvent (Two-Component Formulation)

Component (1):
0.5 of polyethylene oxide PEO-1500 are dissolved in 300 ml of a 10% solution of dextran having a molecular weight of 40 kDa in a 0.025 M sodium phosphate buffer with pH 8.2, 5.7 g of protosubtilin G3Kh are added, the mixture is stirred at a temperature of 18-20° C. for 30 minutes. Then ballast proteins are precipitated by salt precipitation techniques. For this to be done, added to the mixture in succession till complete dissolution are 1.3 g of sodium phosphate disubstituted to final concentration of 0.45% and 1.9 g of calcium chloride to final concentration of 0.63%. After the dissolution of calcium chloride an insoluble precipitate of calcium phosphate is formed in the reaction mixture, and this calcium phosphate adsorbs the ballast proteins. The mixture is maintained for 12 hours at a temperature of 4 to 8° C. for complete precipitation of the ballast proteins. After that the reaction mixture is filtered through paper filters ("white ribbon"). The volume of the filtrate is 300 ml. The obtained solution is subjected to gamma irradiation in a dose of 1.0 Mrad. After the irradiation the solution is subjected to sterilizing filtration, packaged in batches of 10 ml in 15 ml vials and lyophilized to a residual moisture content not exceeding 2%. As a result, component (1) of the composition is obtained, having the following formulation in weight percent:

| 1. | Protosubtilin G3Kh | 1.9 |
|---|---|---|
| 2. | Dextran (molecular weight 40 kDa) | 10.0 |
| 3. | Polyethylene oxide PEO-1500 | 0.5 |
| 4. | 0.025 M sodium phosphate buffer | 87.6 |

The proteolytic activity of component (1) is 750 PU/g.
Component (2) (Solvent):
15.0 g of polyethylene oxide PEO-1500 are dissolved in 300 ml of a 0.025 M sodium phosphate buffer. Then the solution is filtered through paper filters ("white ribbon"). The volume of the filtrate is 300 ml. The obtained solution is subjected to gamma irradiation in a dose of 1.0 Mrad. After the irradiation the solution is subjected to sterilizing filtration and packaged in batches of 10 ml in 15 ml vials. As a result, component (2) of the composition is obtained, having the following formulation in weight percent:

| 1. | Polyethylene oxide PEO-1500 | 5.0 |
|---|---|---|
| 2. | 0.025 M sodium phosphate buffer | 95.0 |

The dissolution of component (1) in the solvent (component (2)) and lyophilization give the claimed pharmaceutical composition.

EXAMPLE 9

Investigation of the Pharmacological Properties of the Claimed Composition ("Trombovazim")

The pharmacological properties of the claimed composition (its conditional appellation being "Trombovazim") have been checked under laboratory conditions in vitro and in vivo.

Figure 1:
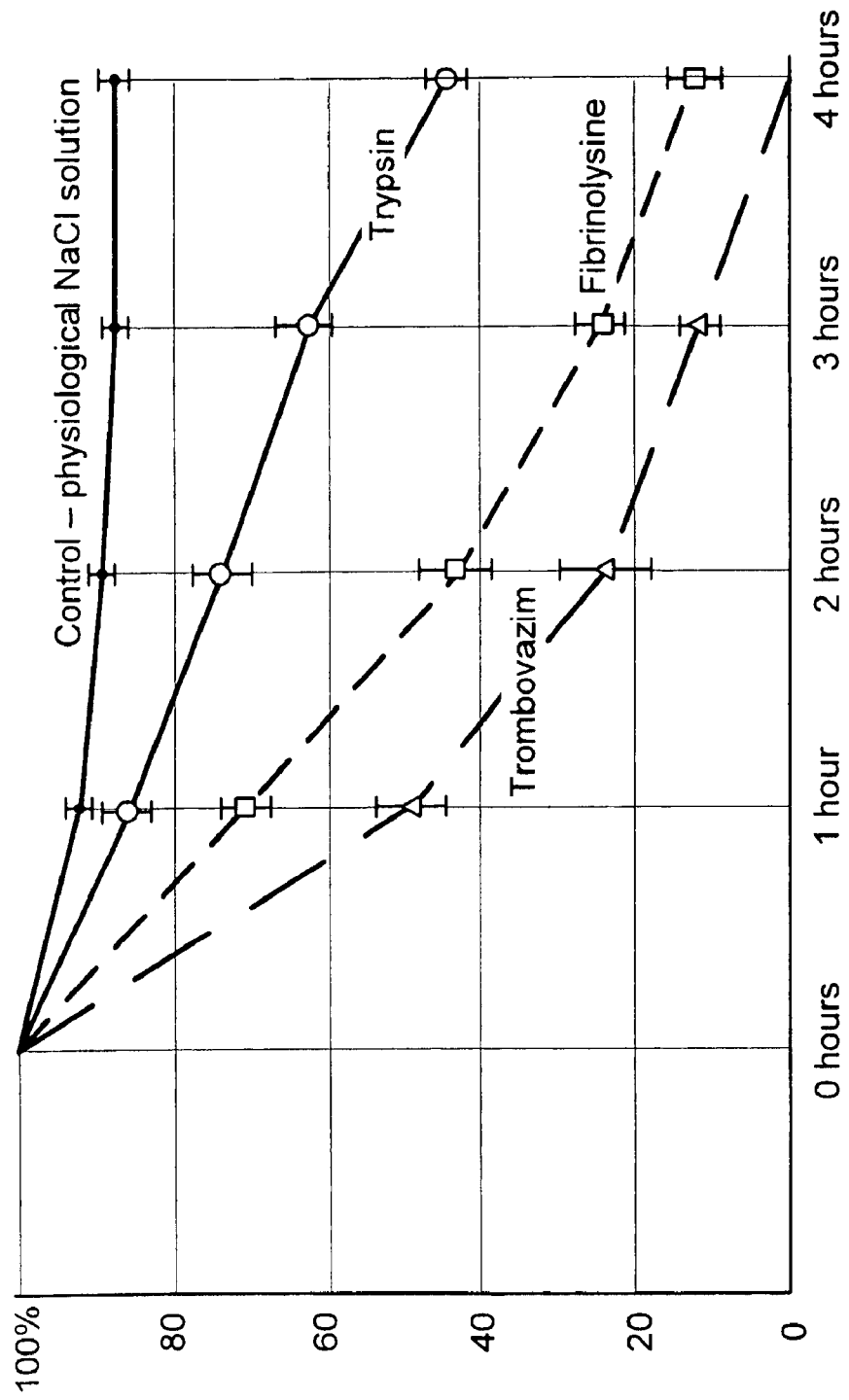
FIG. 1 demonstrates the thrombolytic properties of the claimed composition, investigated on a model of thrombolysis in vitro.

The thrombolytic properties of the composition have been investigated on a model of thrombolysis in vitro (FIG. 1). As can be seen from FIG. 1, "Trombovazim" produces a sharply pronounced thrombolytic effect, reliably exceeding in the standard therapeutic concentration of 50 PhU/ml the effect of fibrinolysine ($p<0.02$); trypsin ($p<0.01$); and spontaneous thrombolysis in physiological solution ($p<0.01$). It should be noted that as the "age" of the thrombus increases to 7 days, the thrombolytic properties of "Trombovazim" are preserved (FIG. 2), while fibrinolysine practically does not act on the 7-days thrombus. During the first two hours the action of fibrolysine does not differ with certainty from the spontaneous background lysis in physiological solution. By the end of the 4th hour the claimed composition dissolves the thrombus completely, while fibrinolysine lyses only 20% of the mass of the "old" thrombus.

It is known that fibrinolysine is the most active fibrinolytic (2), while such preparations as streptokinase, urokinase, alteplase and tissue plasminogen activator are indirect fibrinolytics and their thrombolytic action is mediated by the activation of the fibrinolysis system and production of endogenous fibrinolysine, the latter leading to the lysis of the formed thrombus (1).

The specific thrombolytic activity of "Trombovazim" in vivo has been investigated on a model of carotid artery thrombosis induced in rats by the application of ferrous chloride.

The results of the effect of prophylactic administering "Trombovazim" (80 PU per animal) on the blood flow (ml/min) along ipsilateral carotid arteries after the application of ferrous chloride (0-15 min) in Wistar line rats are presented in Table 2.

the effect of ferrous chloride thereon. Besides, histological (morphometric) investigations have shown that upon therapeutic administration of "Trombovazim" after 24 hours the proportion of animals with complete occlusion of the carotid artery and with the presence of a thrombus in it reduces 3-fold, this being indicative of a pronounced thrombolytic activity of the preparation.

The anti-inflammatory properties of the claimed composition have been investigated on a model of inducing one of the main inflammation mediators—tumor necrosis factor ($\alpha$TNF) in mice of the CBA line with endotoxic shock (FIG.

TABLE 2

| Group | 0 min | 15 min | 30 min | 45 min | 60 min | 75 min | 90 min |
|---|---|---|---|---|---|---|---|
| Control n = 9 | 3.8 ± 0.3 | 2.3 ± 0.4 | 0.9 ± 0.5 | 0.4 ± 0.2 | 0.5 ± 0.4 | 0.2 ± 0.1 | 0.2 ± 0.1 |
| Experiment n = 10 | 2.9 ± 0.3 | 2.5 ± 0.1 | 2.1 ± 0.3 | 1.9 ± 0.4 | 1.9 ± 0.5 | 1.9 ± 0.4 | 1.7 ± 0.4 |

As is seen from the presented results, prophylactic administration of "Trombovazim" effectively limits the process of thrombosis in the carotid artery during the first 1.5 hours after the effect of ferrous chloride thereon.

The results of the effect of therapeutic administering "Trombovazim" (80 PU per animal) on the blood flow (ml/min) along ipsilateral carotid arteries after the application of ferrous chloride (0-15 min) in Wistar line rats are presented in Table 3.

3). The activity of the $\alpha$TNF was measured biologically, using L929 line cells and was expressed in units of action (UA). Shown in FIG. 3 are: the $\alpha$TNF activity in intact animals (1) and in animals after endotoxin administration (2). The administration of "Trombovazim" one hour before the administration of endotoxin (3) reduces 50-fold the $\alpha$TNF activity, this proving the anti-inflammatory properties of "Trombovazim".

TABLE 3

| Group | 0 min | 15 min | 30 min | 45 min | 60 min | 75 min | 90 min |
|---|---|---|---|---|---|---|---|
| Control n = 8 | 3.3 ± 0.4 | 2.6 ± 0.6 | 2.8 ± 0.9 | 2.1 ± 0.7 | 2.3 ± 0.7 | 1.2 ± 0.4 | 0.9 ± 0.4 |
| Experiment n = 9 | 3.8 ± 0.3 | 3.3 ± 0.5 | 2.7 ± 0.5 | 1.7 ± 0.4 | 1.6 ± 0.3 | 1.6 ± 0.4 | 1.8 ± 0.4 |

As is seen from the presented results, therapeutic administration of "Trombovazim" effectively inhibits the process of thrombosis in the carotid artery during the first 1.5 hours after The cytoprotective properties of "Trombovazim" have been studied on a model of indomethacin gastropathy (Table 1) and adrenaline myocarditis in rats (FIG. 4).

TABLE 1

| No. of animal in group | Control: 6.2 mg of indomethacin administered intragastrically 1 hour before experimental effect of intraperitoneal administration of 3 ml of physiological solution | | | Experiment: 6.2 mg of indomethacin administered intragastrically 1 hour before experimental effect of intraperitoneal administration of 3 ml of "Trombovazim" | | |
|---|---|---|---|---|---|---|
| | $S_{stomach}$, mm² SH | $S_{bleeding}$, mm² SB | % of injuries, S% | $S_{stomach}$, mm² SH | $S_{bleeding}$, mm² SB | % of injuries, S% |
| 1 | 910 | 17.3 | 1.9 | 830 | 29.2 | 3.5 |
| 2 | 685 | 26.9 | 3.9 | 778 | 13.6 | 1.8 |
| 3 | 650 | 24.0 | 3.7 | 845 | 12.2 | 1.4 |
| 4 | 784 | 18.4 | 2.3 | 745 | 8.54 | 1.1 |
| 5 | 726 | 34.3 | 4.7 | 823 | 7.6 | 1.1 |
| 6 | 927 | 22.7 | 2.5 | 769 | 0 | 0 |
| 7 | 699 | 46.6 | 6.7 | 778 | 0 | 0 |
| 8 | 853 | 17.0 | 2.0 | 575 | 10.2 | 1.8 |
| 9 | 892 | 34.1 | 3.8 | 653 | 16.2 | 2.4 |
| 10 | — | — | — | 568 | 0 | 0 |
| X ± SD | 792 ± 106 | 26.8 ± 9.9 | 3.5 ± 1.5 | 715 ± 151 | 9.8 ± 9.0 | 1.3 ± 1.2 |

From the presented Table it follows that the control and experimental groups of the rats are comparable in terms of the total stomach area (SH): there was no reliable difference between the characteristics. The area of bleedings (SB) in the groups reliably differed: in the group with preliminary administration of "Trombovazim" (experiment) SB is 3 times smaller than in control (p<0.01). The same reliable relationship is observed when comparing the relative affected area (S %). Hence, "Trombovazim" displays a pronounced cytoprotective effect in the case of indomethacin injury of the stomach mucosa.

FIG. 4 shows the data of histological morphometric investigation of the volume of necroses and dystrophic changes in the myocardium of rats with adrenaline myocarditis. The volume of injuries was determined planimetrically and expressed in percent of the volume density which is equal to the volume of injuries/total value of tissue ratio multiplied by 100%. In the control group (K), after administering adrenaline, 1.0 ml of isotonic NaCl solution was administered intraperitoneally twice a day; in the experimental group (TRB) 1 ml of "Trombovazim" was administered intraperitoneally twice a day. From the presented results it follows that after the development of adrenaline myocarditis the treatment with "Trombovazim" reliably reduces 1.5-fold the number of necroses in the cardiac muscle by the end of the 3rd day: (TBR necr.) compared with control K necr.). Dystrophic changes in the cardiac muscle in the experimental group (TBR dystr.) by the end of the 7th day are reliably 2.5 times smaller than in the control group (K dystr.).

The results presented in Table 1 and in FIG. 4 prove that "Trombovazim" has pronounced cardioprotective and cytoprotective activity. The protective effect of "Trombovazim" reliably manifests itself in specific gastropathy caused by non-steroidal anti-inflammatory preparations, particularly by indomethacin, and the therapeutic effect of "Trombovazim" reliably manifests itself in acute adrenaline myocarditis, in whose pathogenesis the key role is played by acute ischemia, necrosis with the development of myocardial dystrophy.

The disintoxication, anti-ischemic and cytoprotective effects were investigated also on a model of the liver ischemia/reperfusion. For this purpose, in the experimental and control groups of Wistar line rats (10 rats in each group) the liver triad in the animals after laparotomy was clamped for 20 minutes, i.e., the regional lymph and blood circulation were completely blocked. Then the blood flow was restored, and the histological structure of the liver in the animals was investigated (the main quantitative criterion was the accumulation of leukocytes in regional lymphatic nodes as the characteristic of response to the cytotoxic injury of the liver tissue by the products of ischemia/reperfusion: peroxides and free radicals). The results of the investigation are presented in FIG. 5.

As is seen from the presented results, "Trombovazim" produces a hepatoprotective effect on the model of liver ischemia/reperfusion, and this is an additional confirmation of the cytoprotective, disintoxication and anti-inflammatory properties of "Trombovazim".

Though the description of the present invention is commendatory for the preferable use thereof, it should be understood that various modifications may be made therein without departing from the true spirit of the present invention. Therefore, the invention is limited only by the following set of claims.

The invention claimed is:

1. A composition comprising a plurality of active proteases immobilized on a mixture of water-soluble polymers comprising polyethylene oxide and dextran, said plurality of proteases being immobilized on the polyethylene oxide and dextran by irradiating with ionizing radiation an aqueous solution comprising the plurality of proteases and the mixture of water-soluble polymers to immobilize the plurality of proteases on the polyethylene oxide and dextran simultaneously, each of said plurality of proteases being capable of selectively degrading a thrombogenic protein and said plurality of proteases being capable of hydrolyzing a greater variety of peptide linkages than each of the proteases individually.

2. A composition according to claim 1, wherein the ionizing radiation is selected from the group consisting of a flow of accelerated electrons, gamma-radiation and UV-radiation.

3. A composition according to claim 1, wherein each of the plurality of proteases is from a microbiological, animal or vegetable starting material.

4. A composition according to claim 3 wherein each of the plurality of proteases is produced by *Bacillus subtilis*.

5. A composition according to claim 1, in combination with an anti-inflammatory selected from the group consisting of aspirin, indomethacin and diclofenac.

6. A composition according to claim 1, wherein the plurality of proteases immobilized are lyophilized active proteases.

7. A method comprising providing the composition according to claim 1, and administering the composition to a patient in an effective therapeutic amount for treating a disease selected from the group consisting of: ischemic heart disease, acute myocardial infarctions, ischemic disturbances of cerebral circulation, arterial thromboses, venous thromboses, obstructive diseases of the lungs, gastrites and stomach ulcer, gynecological disease, and stomatological disease.

8. The method according to claim 7, wherein the composition is administered to the patient by a mode selected from the group consisting of parenteral, oral, intracavitary and local administration.

9. A composition according to claim 1 further comprising a non-steroidal analgesic.

10. A composition according to claim 1, wherein the radiation is a flow of accelerated electrons or gamma-radiation.

11. A composition according to claim 1, wherein the plurality of proteases comprise subtilysine.

* * * * *